(12) United States Patent
Rinne

(10) Patent No.: US 6,241,973 B1
(45) Date of Patent: Jun. 5, 2001

(54) METHOD AND PRODUCT FOR CLEANING AND/OR WHITENING OF TEETH

(76) Inventor: Ari Rinne, Pajutie 3 B, FIN-2G900 Turku (FI)

( * ) Notice: Subject to any disclaimer, the term of this patent is extended or adjusted under 35 U.S.C. 154(b) by 0 days.

(21) Appl. No.: 09/331,777

(22) PCT Filed: Jan. 2, 1998

(86) PCT No.: PCT/FI98/00001

§ 371 Date: Jun. 24, 1999

§ 102(e) Date: Jun. 24, 1999

(87) PCT Pub. No.: WO98/29088

PCT Pub. Date: Jul. 9, 1998

(30) Foreign Application Priority Data

Jan. 3, 1997 (FI) .......................................... 970012

(51) Int. Cl.[7] ................. A61K 7/28; A61K 7/16

(52) U.S. Cl. .............................. 424/50; 424/49

(58) Field of Search .......................... 424/49–58

(56) References Cited

FOREIGN PATENT DOCUMENTS

| | | |
|---|---|---|
| 959764 | 12/1974 | (CA) . |
| 2714718 | 10/1977 | (DE) . |
| 96743 | * 5/1996 | (FI) . |
| 4675 | * 1/1968 | (FR) . |
| 1448385 | * 8/1993 | (FR) . |
| 8-157352 | 6/1996 | (JP) . |
| 96 07324A1 | * 3/1996 | (WO) . |
| 97 11722A1 | * 4/1997 | (WO) . |
| 9829088A1 | * 7/1998 | (WO) . |
| 9937283A1 | * 7/1999 | (WO) . |

OTHER PUBLICATIONS

Lyon, Jr. et al., "Evaluation of Effects of Application of a Citroxain–Containing Dentrifice," 3 *J. Esthetic Dentistry* 51–53 (1991).
Kirschke et al., *Lysomal Cysteine Proteinases* (2d ed. 1998).
Abrahamson, "Human Cysteine Proteinase Inhibitors," ?*Scand. J. Clin. Lab. Invest. Suppl.* 191: 21–23 (1988).
Bromme et al., "Tight-binding Inhibition of Cathepsin S by Cystatins," 50 *Biomed. Biochim.Acta* 4–6, 631–635 (1991).
Saettone et al., "Evaluation of Muco–adhesive Properties and In Vivo Activity of Opthalmic Vehicles Based On Hyaluronic Acid," 51 *Int. J. Pharmaceutics* 203–212 (1989).
Lee et al., "Ocular Drug Bioavailability From Topically Applied Liposomes," 29 *Survey of Ophthalmology* 335–348 (1985).
Longer et al., "Fundamental Aspects of Bioadhesion," 7 *Phar. Int.* 114–117 (1986).
Hui et al., "Ocular Delivery of Progesterone Using A Bioadhesive Polymer," 26 *Int. J. Pharmaceutics* 203–213 (1985).

Bjorck et al., "Bacterial Growth Blocked By A Synthetic Peptide Based on the Structure of a Human Proteinase Inhibitor," 337 *Nature* 385 (1989).
Meisner et al., "Liposmal Ophthalmic Drug Delivery. III. Pharmacodynamic and Biodisposition Studies of Atropine," 55 *Int. J. Pharmaceutics* 105–113 (1989).
Barber et al., "Tear–induced Release of Liposome–entrapped Agents," 60 *Int. J. Pharmaceutics* 219–227 (1990).
Suominen et al., "Cathepsin B' in the Thyroid Gland," 25 *Acta. Chem. Scand.* 2531 (1971).
Rinne et al., "Demonstration of Cathepsins H and L in Rat Tissues," 45 *Biomed. Biochim. Acta.* 1465–1476 (1986).
Nakamura et al., "An Endogenous Inhibitor of Calcium–activated Neutral Proteinases in UMX 7.1 Hamster Dystrophy," 14 *Muscle & Nerve* 701–708 (1991).
Hayashi, "The Intracellular Neutral SH–Dependent Protease Associated With Inflammatory Reactions," 40 *Int. Rev. Cytol.* 101–151 (1975).
Rinne et al., "Uber das Vorkommen des Epidermalen SH–Proteases–Inhibitors im Lymphatischen Gewebe," 75 *Verh. Anat. Ges.* 573–74 (1981).
Isemura et al., "Characterization and Amino Acid Sequence of a New Acidic Cysteine Proteinase Inhibitor (Cystatin SA) Structurally Closely Related to Cystatin S, From Whole Human Saliva," 102 *J. Biochem.* 693–704 (1987).
Jarvinen et al., "Partial Purification and Some Properties of a New Papain Inhibitor From Psoriatic Scales," 82 *J. Invest. Dermatol.* 471–476 (1984).
Rinne, "Cystatin A," *Human Protein Data* 3 Installment (A. Haeberli ed. 1995).
Bjorck et al., "Cystatin C, A Human Proteinase Inhititor, Blocks Replication of Herpes Simplex Virus," 64 *J. Virol* 941–943 (1990).
Smolin et al., "Idoxuridine–liposome Therapy for Herpes Simplex Keratitis," 91 *Am. J. Ophthalmol.* 220–225 (1981).
Guo et al., "Bioadhesive Liposomes in Ophthalmic Delivery," 28 *Invest. Ophthalmol Vis. Sci. Supp.* 72 (1987).
Finne, "Basic Salts Modify Timolol Delivery in Ocular Inserts of Alkyl Monesters of Poly(vinyl methyl ether–maleic anhydride)," *Univ. Kupio Research Reports* 15 (1991).
Lahdes, "Systemic Absorption and Effects of Topically Applied Ocular Anticholinergic Drugs," *Annales Universitatis Turkuensis* Ser. D, Tom. 218 (1996).

(List continued on next page.)

*Primary Examiner*—Shep K. Rose
(74) *Attorney, Agent, or Firm*—James C. Lydon

(57) ABSTRACT

A method and a product for cleaning and/or whitening of teeth. Natural human cysteine proteinases are employed for cleaning and whitening purposes and this activity can be blocked by natural cysteine protease inhibitors, which are released secondarily from the product at a later stage. The use of natural cysteine proteinases and their inhibitors provides the advantage that they are man's own proteins, and therefore the risk of allegorization is minimized. In addition, their enzyme kinetics are will known.

12 Claims, No Drawings

OTHER PUBLICATIONS

Huupponen et al., "The Effect of Some Macromolecular Ionic Complexes on the Pharmaco–kinetics and dynamics of Ocular Cyclopentolate In Rabbits," 8 *J. Ocul. Pharmacol.* 59–67 (1992).

Kupferman et al., "Prolongation of Anti–Inflammatory Effect of Prednisolone Acetate. Influence of Formulation in High Viscosity Gel," 99 *Arch. Ophthalmol.* 2028–2029 (1981).

Lewis et al., "Ethoxzolamide Analogue Gel. A Topical Carbonic Anhydrase Inhibitor," 102 *Arch. Ophthamol.* 1821–1824 (1984).

Kirschke et al., "Cathepsin S From Bovine Spleen. Purification, Distribution, Intracellular Localization and Action on Proteins," 264 *J. Biochem.* 467–473 (1989).

Jarvinen et al., "Human Spleen Cysteine Proteinase Inhibitor. Purification, Fractionation Into Isolelectric Variants and Some Properties of the Variants." 708 *Biochim. Biophys. Acta.* 210–217 (1982).

Jarvinen et al. "Alpha–N–Benzoylarginine–2–Naphthylamide Hydrolase (Cathepsin B?) From Rat Skin. II. Purification of the Enzyme and Demonstration of Two Inhibitors in the Skin," 29 *Acta. Chem. Scand. B* 772–780 (1975).

Green et al., "Cystatin–like Cysteine Proteinase Inhibitors From Human Liver," 218 *J. Biochem.* 939–946 (1984).

Rinne, "Epidermal SH–proteinase Inhibitor. Occurrence in Human and Rat Tissues and in Human Neoplasms," *Acta. Univ. Ouluensis* Ser. D, Medica No. 41 (1979).

Rinne et al., "Cystatin B," *Human Protein Data* 3 Installment (A. Haeberli ed. 1995).

Davies et al., "Immunolocalization of Human Cystatins in Neutrophils and Lymphocytes," 80 *Histochemistry* 373–377 (1984).

Bjorklund et al., "Rhabdovirus–Induced Apoptosis in a Fish Cell Line is Inhibited by a Human Endogenous Acid Cysteine Proteinase Inhibitor," 71 *J. Virol* . 5658–5662 (1997).

* cited by examiner

METHOD AND PRODUCT FOR CLEANING AND/OR WHITENING OF TEETH

This application is a 371 of PCT FI98/00001 filed Jan. 1, 1998

The object of the invention is a method and a product for cleaning and/or whitening of teeth based on the use of a cysteine proteinase.

PRIOR ART

Cysteine proteinases and their inhibitors

Cysteine proteinases are proteolytic enzymes which possess a cysteine residue in their active site. For the existence in an active reduced form these enzymes need an external sulfhydryl reagent. The mammalian cysteine proteinases belong to the cathepsin family and among them at least cathepsins B, H, L, S, O, U, and N have been purified and classified. The first mammalian cysteine proteinase to be characterized was cathepsin B (Suominen, J. & Hopsu-Havu, V. K.: Cathepsin B in the thyroid gland. Acta chem. Scand. 1971:25:2531). These are distributed throughout the body but they are found especially in the kidneys, liver, and macrophages (Rinne, A., Järvinen, M., Kirschke, H., Wiederanders, B., Hopsu-Havu, V. K.: demonstration of cathepsins H and L in rat tissues. Biomed Biochim Acta 1986:45:11–12:1465–1476). A part of them are active in acidic pH values but a part are active in physiological pH values, such as cathepsin s. (Kirschke, H., Wiederanders, B., Brömme, D., Rinne, A.: Cathepsin S from bovine spleen. Purification, distribution, intra cellular localization and action on proteins. Biochem J 1989:264:467–473, and Kirschke, H., Rawlings, N. D. , Barrett, A. J.: Lysosomal cysteine proteinases. Academic Press, London 1995.

In the plant kingdom, there are found cysteine proteinases such as ficin, bromelain and papain (Jävinen, M., Rinne, A.: Human spleen cysteine proteinase inhibitor. Purification, fractionation into isoelectric variants and some properties of the variants. Biochim Biophys Acta 1982: 708: 210–217).

The cysteine proteinases in the plant kingdom and those found in mammalians are closely related to each other. Papain is classically used in research work as a cysteine proteinase employed routinely in tests and as a proteinase for comparative research work concerning mammalian cysteine proteinases and their inhibitors. (the reference books, the inventor's own unpublished and published results (Ari Rinne and Mikko Järvinen 1976–1997)).

The most numerous and best known mammalian cysteine proteinases are considered to belong to the cathepsin family. However, the mammalian cysteine proteinase inhibitors are divided into several families by their structure and mode of action.

Among the mammalian cysteine proteinases are further known calcium-activated cysteine proteinases, which are considered to belong to the calpain family. Their inhibitors are called calpastatins (M. Nakamura, s. Imajoh-Ohmi, K, Suzuki and S. Kawashima: An endogenous inhibitor of calcium-activated neutral proteinase in UMX 7.1 Hamster Dystrophy. Muscle & Nerve 14: 701–708, 1991). They are also inhibited by the cathepsin inhibitor kininogen.

Cysteine proteinases have the property of dissoluting biological material, which properties can be inhibited by using inhibitors (toothpastes Rembrant ® and Yotuel®, Kirschke, H., Rawlings, N. B., Barrett, A. J.: Kysosomal cysteine proteinases, Academic Press, London 1995 and the inventor's own unpublished results.)

The following are the most important and best known so called "classical" natural (originating form the body) families of cysteine proteinase inhibitors:

1. Epdiermal-SH-proteinase inhibitor or acid cysteine proteinase inhibitor (ACPI) or stefin A. This inhibitor was simultaneously discovered in the beginning of the 1970'ies by Hayashi and Järvinen (Hayashi, H. (1975): The intra cellular neutral SH-dependent protease associated with inflammatory reactions. Int. Rev. Cytol., 40:101–151; Jävinen, M. and Hopsu-Havu, V. K. (1975): α-N-Benzoly-arginine-2-naphthylamide hdyrolase (Cathepsin B1?) from rate skin. II. Purification of the enzyme and demonstration of two inhibitors in the skin. Acta Chem Scand B, 29: 772–780). It is aimed to have this inhibitor named internationally as cystatin A. (Type I) (Rinne, A: Cystatin A. Human protein data [A. Haeberli, editor, VCH Verlag, Weinheim], 3. Installment 1995; Green, G. D. J., Kembhavi. A. A. , Davies, M. L., Barrett, A. J. : Cystatin-like cysteine proteinase inhibitors from human liver. Biochem J 1984: 218: 939–946; Rinne, A.: epidermal SH-protease Inhibitor. Occurrence in human and rat tissues and in human neoplasms Thesis. Acta Univ Ouluensis, Ser D. Medica No. 41, Oulu 1979).

2. Another small-molecular cysteine proteinase inhibitor, which was electroneutral at pH-values 6.0–65., was discovered at the end of the 1970'ies (A. Rinne, M. Järvinen, J. Martikainen, M. Alavaikko und O. Räsänen: Über das Vorkommen des epidermalen SH-Protease-Inhibitors im lymphatischen Gewebe. Verh. anat. Ges. 75, S. 573–574 (1981): Järvinen, J., Rinne, A.: Human spleen cysteine proteinase inhibitor. Purification, fractionation into isoelectric variants and some properties of the variants. Biochim Biophys Acta 1982: 708: 210–217). Neutral cysteine proteinase inhibitor (NCPI) or cystatin B or stefin B. (Type I) (Rinne, A., Rinne, R., Jävinen, M.: Cystatin B. Human protein data [A. Haeberli, editor, VCH Verlag, Weinheim], 3. Installment 1995).

3. γ-trace, which is called cystatin C. (Type II) (Abrahamson, M.: Human cysteine proteinase inhibitors. Isolation, physiological importance, inhibitory mechanism, gene structure and relation to hereditary cerebral hemorrhage. Scand J Clin Lab Invest 1988: 48: suppl 191: 21–31).

4. Cystatin S. (Type II) (Isemura, S., Saitoh, E., Sanada, K.: Characterization and amino acid sequence of a new acidic cysteine proteinase inhibitor (Cystatin SA) structurally closely related to cystatin S, from human whole saliva. J. Biochem 1987: 102:693–704).

5. Kininogen. (Type III). (Järvinene, M., Hopsu-Havu, V.-K.: α-N-benzoylarginine-2-naphyhylamide hydrolase (cathepsin B1?) form rat skin. II. Purification of the enzyme and demonstration of tow inhibitors in the skin. Acta Chem Scand 1975: B:29:772–780).

6. "Psoriasis inhibitor", for which we have recently proposed the name squamin. (Type ? (not classified so far) (J ärvinen, M., Rinne, A., Hopsu-Havu, V. K. : Partial purification and some properties of a new papain inhibitor from psoriatic scales, J Invest Dermatil 1984:82473–476).

The type I lacks sulfur birdges. The type II has two sulfur bridges. The type III has three structures of the type II and a chain responsible for kininogen activity. Cysteine proteinase inhibitors are found particularly in cellular structures which have a role in the defense mechanism, such as in granulocytes, stratified squamous epithelia, dendrites as well as in histiocytic reticular cells and in the reserve cells in prostata. (Davies, M. E. and Barrett, A. J.. Immunolocalization of human cysteins in neutrophils and lymphocytes. Histochemistry, 80: 373–377, 1984). In addition to the natural cysteine proteinase inhibitors, also synthetic peptide cysteine proteinase inhibitors have been made. (Brömme, D., Rinne, R., Kirschke, H.: Tight-binding inhibition of cathepsin S by cystatins. Biomed Biochim Acta 1991: 150:631–635). cysteine proteinase inhibitors are also found in the skin of poikilothermic animals, such as salmon and river lamprey (for example the recently found so called troms family; the inventor's own unpublished results). Cysteine proteinase inhibitors are known to inhibit the reproduction of microbes (bacteria and viruses) and/or the associated destruction of tissues (Rinne, A.: Cystatin A. Human protein data [A. Haeberli, editor, VCH Verlag, Weinheim], 3. Installment 1995; Björck, L., Grubb, A. and Kjellen, L. (1990) Cystatin C, a human proteinase inhibitor, blocks replication of Herpes simplex virus. J Virol 64, 941–943Björck, L., Akesson, P., Bohus, M., Trojnar, J., Abrahamson, M., Olafson, I., and Grubb, A. (1989) Bacterial growth blocked by a synthetic peptide based on the structure of a human proteinase inhibitor. Nature 337, 385–386Björklund, H. V., Johansson, T. R., and Rinne, A. Rhabdovirus-induced apoptosis in a fish cell line is inhibited by a human endogenous acid cysteine proteinase inhibitor. J Virol, 71: 5658–5662, 1997).

Of course, the human cysteine porteinase inhibitors found endogenously in the mouth (in the saliva and the mucosa) make a contribution to the inhibition of cysteine proteinases. However, the ACPI, for example, is known to be reduced or lost in an inflamed or cariotic mouth (Finnish patent FI 96743 and inventor's own unpublished results).

Controlled release of an active agent from a pharmaceutical preparation

Controlling the rate and timing of the release of an active agent, generally a medicament, form a pharmaceutical preparation is a common practice in the development of drugs. The controlled release of an active agent is applied, for example, for preparations which do not withstand the action of the gastric juice. In that case a tablet is coated with a membrane which is not degraded until in the small intestine, in which case the drug can be protected against the deleterious effects of the acidic environment in the stomach. Many kinds of pharmaceutical preparations, in which the drug is released at a controlled rate, are also used in ophthalmology. The aim in their development has been to obtain a relatively slow release of the drug from the carrier. However, by the choice of a suitable form of preparation it is possible to control the rate of release in both directions. When the so called pro-drugs are used, the drug itself is bound to a carrier in such a manner that the complex is inactive and the activation does not occur until, for example, at the mucosa upon the cleavage of the bond between the carrier and the drug. Examples of such preparations are among others piv- and bacampicillin, both of which are clinically used preparation. The drug can also be activated by the pH in its environment. A well known example of this is omeprazole, a drug which is used in the treatment of gastric ulcer which does not become active until upon contact with the hydrogen ion-producing parietal cells.

The pharmaceutical dosage form of a drug can be designed to release the active agent relatively quickly in the oral mucosa. For example, upon the delivery of nitroglyserin as a resoriblet or a sublingual tablet, the originally solid preparation disintegrates on the oral mucosa at a conspicuously fast rate such that the effect of the drug in the bloodstream is obtained as early as in 2–3 minutes. For the treatment of gastric ulcer is available on the market among others Pepcidin Rapitab tablet (MSD), which rapidly releases the drug upon contact with oral excretions; the dissolution of the tablet on the oral mucosa takes only a few tens of seconds. A two-layered tablet allows the release of desired pharmacologically active agents in a chosen order. The outer layer of the tablet can be adapted to dissolve rapidly upon contact with oral excretions, whereupon the agent mixed therein is delivered quickly in the mouth; by employing excipients in the core of the tablet, the core can be adapted to dissolve at a slower rate, which results in a slower release and a slower onset of the effects of the active agents mixed therein. By using normal pharmaceutical practice it is also possible to produce preparations comprising more than two layers, which result in the ability to control the respective order of release and the onset of the effects of the active agent when the product is held on the oral mucous membrane.

Liposome technique

The mixing of molecules with hydrophilic and hydrophobic properties in an aqueous solution produces vesicles, known as liposomes. The liposomes allow the encapsulation of, among other things, drugs and many other biologically active agents within their interior, thereby making it possible to have a desired influence on the spectrum of actions of the respective agent in the body. The composition of the liposomal membrane, encapsulation efficiency or the ability of the liposome to encapsulate the desired active agent within its interior, the stability of the preparation, the release rate of the active agent, the distribution of the liposome and its surface electric body, the size of the liposome and its surface electric charge contribute, besides of other factors, to the properties of the complex composed of the liposome and the encapsulated agent, thereby making the application of the combination in various situations flexible, Insulin can be mentioned as an example of a protein structure which is rather simple to encapsulate in the liposome. On the inner surface of a production vessel a thin membrane can be made of lechitin and cholesterol. The addition of a water-based buffered insulin solution and subsequent shaking results in the formation of insulin-containing liposomes. Various liposome preparations far available commercially and are used widely, for example in skin care products. Catezomes TM (Collaborative Laboratories) can be mentioned as an exemplary product which can be used in the encapsulation of both hydrophilic and hydrophobic agents and which are specially designed to keep the active agent on the surface of the skin.

The problem associated with the cysteine proteinase preparations in the art

The enzymatic activity of cysteine proteinases has been exploited in the art in a cleaning and whitening toothpaste (Rembrandt®, Yotuel®). In this toothpaste papain form the papaya-fruit has been used as a cysteine proteinase. Papain is a foreign protein to the mammalian body and in long term use of it is know to cause allergy at lest. In addition, papain is active at an acidic pH but not at a physiological pH in the oral area, as for example body's own cathepsin S. Similarly, Yotuel® chewing gum, which contains, among other things, xylitol and pain as a whitening agent, has appeared on the market quite recently.

SUMMARY OF THE INVENTION

The invention is directed to a method for cleaning and/or whitening of the teeth of an individual. In the method, body's own cysteine proteinase is contacted with the teeth.

The invention is also directed to an oral hygiene product, which is intended for the cleaning and/or whitening of a person's teeth and which contains a cysteine proteinase and a necessary carrier. According to the invention, the cysteine proteinase is one of the man's own natural cysteine proteinases.

DESCRIPTION OF THE INVENTION

The terms "natural" cysteine proteinase or cysteine proteinase inhibitor and "the body's own" cysteine proteinase or cysteine proteinase inhibitor refer to substances purified by techniques in the art of protein chemistry as well as produced by molecular biological techniques. Most of such cysteine proteinases belong to the cathepsin or calpain family.

In the method of the invention the cysteine proteinase is activated by contacting it with a sulfhydryl reagent, such as cysteine. For the activation, it is also of importance that the pH is suitable to the activation of the respective cysteine proteinase. The pH is suitable adjusted, if necessary, in order to activate the cysteine proteinase. Various procedures are available for the activation.

If desired, cysteine proteinase activity can be blocked by delivering a pH-controlling agent and/or body's own cysteine proteinase inhibitor into the mouth at a moment when the cysteine proteinase has acted sufficiently long. Alternatively, the action of the cysteine proteinase can be blocked by releasing into the mouth a pH-controlling agent given concurrently with the cysteine proteinase and/or body's own cysteine proteinase inhibitor.

The oral hygiene product of the invention, which is intended to cleaning and/or whitening of teeth of an individual and which comprises the body's own cysteine proteinase and a necessary carrier, can, in principle, be of any type. For example, it can be a solid, such as a chewing gum, or a tablet; a solution; a suspension; or semi-solid, such as, for example, a toothpaste.

According to the preferred embodiment, the product comprises also a sulfhydryl reagent or some other reductant necessary for the activation of the cysteine proteinase. If the ambient oral pH is unfavourable for the activation of the cysteine proteinase it is advisable that the product also contains a pH-controlling substance.

If desired, to the product can also be added an agent which blocks the cysteine proteinase and which is released after the completion of the desired duration of action of the cysteine proteinase. The agent which blocks the cysteine proteinase can be a pH-controlling agent (or an agent which blocks the active state of the cysteine proteinase) or any of the body's own cysteine proteinase inhibitors.

The release of the agent which blocks the cysteine proteinase after a specified time has elapsed can be accomplished by employing any of the techniques known in the art of controlled release.

The product can also comprise many of the body's own cysteine proteinases and possible many of the body's own cysteine proteinase inhibitors.

The invention can be described in more detail by reference to the following examples:

To a toothpaste, mouthwash, or candies is added natural human cathepsin S (this can be produced for example by molecular biological techniques), which is active at the physiological pH prevailing in the mouth. A further addition is a sulfhydryl reagent, for example cysteine, which is released in the mouth form granules, see below. With the assistance of an externally added sulfhydryl reagent cathepsin S becomes biologically active and performs proteolytic cleaning and whitening in the mouth and the teeth. The long-term and possibly deleterious activity of cathepsin S is inhibited with the release after a specified time into the mouth of (a) human cysteine proteinase inhibitor(s) added to the product. Also the action of cysteine proteinase inhibitors in inhibiting the growth of pathogenic micro-organisms, which is known in the art, is also taken advantage of. In particular, as cysteine proteinase inhibitors known natural human cysteine proteinase inhibitors are employed.

Alternatively, the products can also be prepared so that, for example, human cathepsins B, H or L are used as the natural cysteine proteinase, in which cases the product has to be made such that the excipients in the product convert the oral mucosa transiently acidic, under which conditions the respective cathepsins are biologically active. Of course, also so called "new" recently discovered human cysteine cathepsins, such as O, U K etc., can be used once their activity ranges have been exactly determined.

All the proteins (cysteine proteinases and their inhibitors) associated with this invention can be produced by purifying them directly form human tissues or by using molecular biological techniques.

The pH in the mixture and in the mouth should return again to a physiological value secondarily in connection with the release of the inhibitor. The potency of the respectively exogenously added natural cathepsins is exhausted and the natural externally added inhibitors together with the inhibitors already present orally secure additionally the cessation of the proteolysis, which is deleterious in the body. The excipients in question (cysteine proteinases and their inhibitors) are added to products which are known per se (toothpastes, mouthwashes, and candy products). Many variations can be made in the basic products. Modifications and fine-tuning can be made by using cysteine proteinases which differ somewhat in their biological properties. Similarly, representatives of various cysteine proteinase inhibitor families can be used.

Cathepsins and the sulfhydryl reagent are packaged into the different phases of the products by employing for example liposomes (the pH is dependent upon the cathepsin employed), from which these are released at a controlled rate as the conditions in the environmental change upon bringing the liposomes into contact with the oral mucosa. The retention time on the mucosa is dependent among other things on their electric charge (positive, neutral, negative). Thus the retention time can be controlled according to the desired goal. (Smolin, G., Okumoto, M., Feiler, S., Condon, D.: Idoxuridine-liposomal therapy for herpes simples keratitis. Am J Ophthalmol 1981:91:220–225; Meisner, D., Pringle, J., Mezei. M.: Loposomal ophthalmic drug delivery. III. Pharmacodynamic and biodisposition studies of atropine. Int J Pharm 198:55:105–113; Barber, R. F., Shek, P. N.: Tear-induced release of liposome-entrapped agents. Int J Pharm 1990:60:219–227; Lee, V. H. L., Urrea, P. T., Smith , R. E., Schantzlin, D. J.: Ocular drug bioavailability from topically applied lipsomes. Surv Ophthalmol 1985:29:335–348; Guo. L. S. S., Redema. C. T., radhakrisnan, R.: Bioadhesive liposomes in ophthalmic deliver. Invest Ophthalmol Vis Sci 1987:28:72; Finne, U.: Basic slats modify timolol delivery in ocular inserts of alkyl monoesters of poly(vinyl methyl ether-maleic anhydride). University of Kuopio, National Agency for Welfare and Health, Research Reprots 15, Helsinki 1991). the secondarily release cysteine proteinase inhibitor is bound for example to a mucoadhesive polymer (the physiological or slightly basic or a pH). These are synthetic or natural macromolecules [Linger, M. A., Robinson, J. R.: fundamental aspects of bioadhesion. Pharm Int 1986:7:114–117; Hui, H. W., Robinson, J. R.: Ocular delivery of progesterone using a bioadhesive polymer. Int J Pharm 1985:26:203–213; Saettone, M. F., Chetoni, P., Torracca, M. T., Burgalassi, S., Giannaccini, B.: Evaluation of muco-adhesive properties and in vivo activity of ophthalmic vehicles based on hyaluronic acid. Int J Pharm 1989:51:203–212; Robinsin, J. R.: Bioadhesive compositions and methods therewith. U.S. Pat. No. 4,983,392 1991; Finne, U.: Basic salts modify timolol delivery in ocular inserts of alkyl monoesters of poly(vinyl methyl ether-maleic anhydride). University of Kuopio, National Agency for Welfare and Health, Research Reports 15, Helsinki 1991; Lahdes, K: Systemic absorption and effects of topically applied ocular anticholinergic drugs, Annales Universitiatis Turkuensis Ser. D, Tom. 218, Turku 1996; Huupponen, R., Kaila, T., Saettone, M. F., Monti, D., Iisalo. e., Salminen, L., Oksala, O.: The effect of some macromolecular ionic complexes on the pharmacokinetics and dynamics of ocular cyclopentolate in rabbits, J Ocul Pharmacol 1992:8:59–57]. This provides a longer lasting inhibitor on the mucous membrane, whereupon the known ability of the cysteine proteinase inhibitors to inhibit the tissue defects caused by for example pathogenic organisms (disease processes) is also specifically enhanced. Liposomes or other similar controlled release structures having mucoadhesive properties can also be used in the package.

A paced action can be obtained also by using a so called hydrogel form which the active agent is slowly released by diffusion (Kupferman, A., Ryan, W. J., Leobowitz, H. M.: Prolongation of anti-inflammatory effect of prednisolone acetate. Influence of formulation in high-viscosity gel. Arch Ophthalmol 1981:99:2028–2029; Lewis, R. A., Schoenwald, R. D., Eller, M. G., Barfknecht, C. F., Phelps. C. D.: Ethoxzolamide analogue gel. A topical carbonic anhydrase inhibitor. Arch Ophthamol 1984:102:1821–1824; Urtti, A.: Silmän uudet lääkemuodot. In: Biofarmasia 1986 Kuipio. Gummerus Oy, Jyväskylä 1986:44–53). If various matrices (carrier phases) are included in the same preparation, the release of active agents admixed therein is accomplished with distinct rates and different duratins of existence on the oral mucosa.

If the product is made into a dry product, such as a chewing gum, the active agents can be package in a layered manner. The pace of the release can be controlled to obtain a more defined and clear result by packaging the active agent sin different materials.

EXAMPLE

Toothpaste

The composition of a toothpaste can be the following:

1. Abrasive and polishing agents, for example calcium carbonate or tricalcium phosphate, ca 50%

2. Binder, for example aqueous silica or sodium carboxymethylcellulose, ca 3%

3. A foam-producing non-soap-based detergent, ca 2%

4. A soap-based detergent ca. 8%

5. Humidifiers, for example sorbitol or glycerol, ca 3%

6. Flavor and aroma, for example saccharine or xylitol (according to current trend salmiac), ca 1%

7. 0,0001% cysteine cathepsin as such or packaged into liposomes 8. 0,0001% cysteine packaged for example in liposomes 9. 0,001% cysteine proteinase inhibitor affixed into a mucoadhesive polymer 10. balance water.

The invention has significant advantages as compared to the products of prior art:

in the same product, natural exogenously delivered cysteine proteinases are used to obtain cleaning and whitening and, on the other hand, the excessive and probably deleterious action upon tissues is blocked by using exogenously added natural cysteine proteinase inhibitors. The enzyme kinetics of theses proteins is well known slightly differing natural cysteine proteinases and their inhibitors can be used, and therefore the action spectrum becomes wide and the influence on the control can be more easily accomplished the temporal control of the active agents has been obtained such that it is sensitive and accurate by employing liposomes, mucoadhesive polymers and hydrogel or other applications of the controlled-release technique the favourable (balancing, anti-inflammatory and antidestructive) effect of the natural inhibitor is not removed immediately from the mucosa in the same product, it is possible to exploit in a controlled manner the beneficial effects of both the cysteine proteinase and their inhibitors both the cysteine proteinases and their inhibitors delivered externally into the body are body's own proteins, therefore the risk of sensitization is small; this is in contrast to the use of the respectively proteinases and their inhibitors, which are recognized as foreign by the body and derived for example from the plant kingdom.

The above mentioned embodiments of this invention are merely examples of the practice of the idea according to the invention. It should be apparent to those skilled in the art that the invention can have various embodiment, which are within the scope of the following claims.

What is claimed is:

1. A method for cleaning and/or whitening of the teeth of an individual, characterized in that a human own cysteine proteinase is contacted with the teeth.

2. The method according to claim 1, characterized in that the cysteine proteinase is activated b contacting it with a sulfhydryl reagent or with an another reducing agent.

3. The method according to claim 2, characterized in that the pH is suitably adjusted, to activate the cysteine proteinase.

4. The method according to claim 1, characterized in that the activity of the cysteine proteinase is blocked by introducing into the mouth either a pH-controlling agent or a human cysteine proteinase inhibitor.

5. The method according to claim 1, characterized in that the activity of the cysteine proteinase is blocked by introducing simultaneously with the cysteine proteinase into the mouth either a pH-controlling agent or a human cysteine proteinase inhibitor.

6. An oral hygiene product, which is intended for the cleaning and/or whitening of the teeth of an individual and which comprises a human cysteine proteinase and pharmaceutically acceptable carrier.

7. The product according to claim 6, characterized in that it comprises a sulfhydryl reagent in an amount effective to activate said human cysteine proteinase and optionally a pH-controlling agent.

8. The product according to claim 6, characterized in that it also comprises an agent for blocking the activity of cysteine proteinase, said agent being released after the desired duration of action of the cysteine proteinase.

9. The product according to claim 8, characterized in that the agent for blocking the activity of cysteine proteinase is a pH-controlling agent.

10. The product according to claim 8, characterized in that the agent for blocking the activity of the cysteine proteinase is a human cysteine proteinase inhibitor.

11. The product according to claim 6, characterized in that it comprises at least two human cysteine proteinases and at least two human cysteine proteinase inhibitors.

12. The product according to claim 6, characterized in that it is in a form selected from the group consisting of a solid; a solution; a suspension; and a semisolid.

* * * * *